United States Patent
Tu et al.

(10) Patent No.: US 6,221,070 B1
(45) Date of Patent: Apr. 24, 2001

(54) STEERABLE ABLATION CATHETER SYSTEM HAVING DISPOSABLE SHAFT

(75) Inventors: Hosheng Tu, Tustin; Weng-Kwen Raymond Chia, Irvine, both of CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 09/295,985

(22) Filed: Jun. 3, 1998

Related U.S. Application Data (63) Continuation-in-part of application No. 08/733,778, filed on Oct. 18, 1996, now abandoned.

(51) Int. Cl.[7] .................................................. A61N 1/05
(52) U.S. Cl. .......................... 606/41; 600/374; 600/585; 600/136; 600/146; 607/122
(58) Field of Search .................. 600/373, 374, 600/377–381, 585, 136, 146; 607/116, 119, 122, 96, 101; 606/41

(56) References Cited

U.S. PATENT DOCUMENTS

| | | | |
|---|---|---|---|
| 4,499,895 | 2/1985 | Takayama | 600/148 |
| 4,519,391 | 5/1985 | Murakoshi | 606/46 |
| 4,534,339 | 8/1985 | Collins et al. | 600/136 |
| 4,911,148 | 3/1990 | Sosnowski et al. | 600/136 |
| 4,919,112 | 4/1990 | Siegmund | 600/136 |
| 5,423,740 | 6/1995 | Sullivan et al. | 604/22 |
| 5,465,733 | 11/1995 | Hinohara et al. | 128/772 |
| 5,487,757 | 1/1996 | Truckai et al. | 607/119 |
| 5,545,200 | 8/1996 | West et al. | 607/122 |
| 5,571,100 | 11/1996 | Goble et al. | 606/41 |

*Primary Examiner*—Linda C. M. Dvorak
*Assistant Examiner*—David M. Ruddy

(57) ABSTRACT

A steerable ablation catheter system suitable for radiofrequency ablation of intracardiac tissue comprises two parts: a disposable catheter shaft with a deflectable tip at the distal end of the shaft; and a handle with steering mechanisms, wherein the two parts are engaged and disengaged through a pair of the quick coupling and locking connecting units.

11 Claims, 8 Drawing Sheets

STEERABLE ABLATION CATHETER SYSTEM HAVING DISPOSABLE SHAFT

CROSS-REFERENCE TO RELATED APPLICATIONS

This application is a continuation-in-part application of U.S. application Ser. No. 08/733,778, entitled "Cardiovascular Catheter System with Exchangeable Handles" filed Oct. 18, 1996, now abandoned, and is incorporated herein by reference.

FIELD OF THE INVENTION

The present invention generally relates to improved constructions for cardiovascular steerable catheters. More particularly, this invention relates to methods and apparatus for mapping electrical potentials within the heart and treating cardiac arrhythmias via a steerable ablation catheter system having a disposable catheter shaft at its distal portion.

BACKGROUND OF THE INVENTION

Symptoms of abnormal heart rhythm are generally referred to as cardiac arrhythmias, with an abnormally slow rhythm being classified as a bradycardia and an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of the heart. The heart includes a number of normal pathways which are responsible for the propagation of signals necessary for normal electrical mechanical function. The presence of arrhythmogenic sites or accessory pathways can bypass or short circuit the normal pathways, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for the physician to be able to accurately steer the catheter to the ablation site. Once at the site, it is important for the physician to control the emission of energy within the body used to ablate the tissue.

Of particular interest to the present invention are radiofrequency (RF) ablation protocols which have been proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable large electrode is introduced to the appropriate heart chamber and manipulated so that the electrode lies right on the target tissue. RF energy is then applied through the electrode to the cardiac tissue in order to ablate a region of the tissue which forms part of arrhythmogenic site or the accessory pathway. By successfully destroying that tissue, the abnormal signal patterns responsible for the tachycardia cannot be sustained.

Catheters utilized in radiofrequency ablation are inserted into a major vein or artery, usually in the neck or groin area, and guided into the chambers of the heart by appropriate manipulation through the vein or artery. The tip portion of the catheter must be steerable by the user from the proximal end of the catheter, so that the electrodes at the distal portion can be positioned against the tissue region to be ablated. The catheter must have a great deal of flexibility in order to follow the pathway of the major blood vessels into the heart, and the catheter must permit user manipulation of the tip portion. In addition, the distal portion of the catheter must be sufficiently resilient in order to be positioned against the wall of the atrium or ventricle and maintained in a contact position during ablation without being displaced by the movement of the beating heart. Along with the steerability, flexibility and resiliency, the catheter must have a sufficient degree of torsional stiffness to permit user manipulation from the proximal end.

Steerable catheters are known for use in a variety of medical procedures. For example, see U.S. Pat. No. 5,318,525 to West, U.S. Pat. No. 5,318,041 to DuBois, U.S. Pat. No. 5,275,151 to Shockey, U.S. Pat. No. 4,998,916 to Hammerslag, U.S. Pat. No. 4,960,134 to Webster, Jr., U.S. Pat. No. 4,944,727 to McCoy, U.S. Pat. No. 4,838,859 to Strassmann, U.S. Pat. No. 4,826,087 to Chinery, U.S. Pat. No. 4,753,223 to Bremer, U.S. Pat. No. 4,685,457 to Donenfeld, U.S. Pat. No. 3,605,725 to Bentov, and U.S. Pat. No. 3,470,876 to Barchilon. Typically, such catheters employ a plurality of steering wires, usually three or more, extending from a steering mechanism at the proximal end of the catheter ("the handle") to an anchor point at the distal portion of the catheter. By tensioning certain of the steering wires from the controller at the handle, the tip portion of the catheter can be manipulated in a desired direction.

A handful of U.S. patents on endoscopes and other apparatus teach the art of disengaging the disposable portion of a device from its more-expensive fixture base, such as a handle station, an imaging station or video display. They include: U.S. Pat. No. 4,519,391 to Murakoshi, U.S. Pat. No. 4,534,339 to Collins et al., U.S. Pat. No. 4,911,148 to Sosnowski et al., U.S. Pat. No. 5,571,100 to Goble et al., U.S. Pat. No. 4,919,112 to Siegmund, U.S. Pat. No. 5,545,200 to West et al., U.S. Pat. No. 5,465,733 to Hinohara et al., U.S. Pat. No. 5,423,740 to Sullivan et al., U.S. Pat. No. 4,499,895 to Takayama and U.S. Pat. No. 5,487,757 to Truckai et al. None of the above-mentioned patents disclose the quick coupling and locking of a disposable catheter shaft to its handle involving the mechanical steering, electrical conducting, and energy delivery wires.

While electrophysiology mapping study and radiofrequency ablation procedure using existing steerable catheters have had promising results, due to potential cross-contamination concerns from a prior patient having AIDS, hepatitis, or unknown diseases, the existing catheter is considered a disposal device and is recommended for one-time use only. Even though certain hospital or clinician might tempt to re-sterilize and re-use the soiled catheter, the re-sterilization process might actually cause the catheter to deform or degrade, and render the catheter less effective and less safe for its intended use. In an electrophysiology procedure, only the catheter shaft portion which contacts human blood and tissue might be potentially contaminated.

In the present medical practices, the whole catheter system including the catheter shaft portion and the handle portion is being discarded. The need for recycle and reuse of the handle portion of a steerable catheter is obvious and makes good sense with respect to health aspects, environmental reasons, cost consideration, and advanced technology of this invention. In a representative steerable electrophysiology catheter, the cost of the handle portion is estimated to be more than four times of the cost of the disposable catheter shaft portion. Though in a previous patent, U.S. Pat. No. 4,911,148 to Sosnowski et al. teaches an endoscope with detachable flexible shaft assembly, it did not disclose a disposable catheter shaft having a mechanical, electrical, and energy delivery wires. The concept of a steerable catheter having a disposable catheter shaft for electrophysiology study and ablation procedure is novel in that the electricity and radiofrequency energy are transmitted through a quick coupling and locking connecting unit.

For these and other reasons, it would be desirable to provide a steerable catheter system suitable for mapping and radiofrequency ablation which has a quick exchangeable connection mechanism. Therefore, a new catheter tubing shaft can be quickly connected to the handle means for electrophysiology procedures.

SUMMARY OF THE INVENTION

The present invention is to provide an improved steerable ablation catheter system of which its catheter shaft can be quickly connected and locked to or disconnected from a handle portion. After use, the catheter shaft can be disengaged from the handle portion and disposed of It is one object of the present invention to provide a catheter which has a disposable catheter shaft. It is another object of the present invention to provide a catheter having a steering mechanism, which has a disposable catheter shaft. It is a further object of the present invention to provide a catheter having electrical wires, energy delivery wires, and steering wires inside the lumen of a catheter, which has a disposable catheter shaft. It is one object of the present invention to provide a catheter having a steering mechanism controlled by an electromechanical device, which has a disposable catheter shaft.

In one embodiment, the catheter system having a connecting unit at the catheter shaft portion and a matching connecting unit at the handle portion. The catheter system comprises a coupling and de-coupling means, wherein a first steering wire, a first conducting wire, and a first energy delivery wire in the connecting unit are quickly coupled and locked to a second steering wire, a second conducting wire, and a second energy delivery wire in the matching connecting unit, respectively, and/or quickly de-coupled.

The method and apparatus of the present invention have several significant advantages over known catheter ablation techniques. In particular, the quick coupling catheter shaft-to-handle provides further advantages and makes good sense with respect to health aspects, environmental reasons, cost consideration, and advanced technology of this invention.

DETAILED DESCRIPTION OF EXEMPLARY EMBODIMENTS

Figure 1:
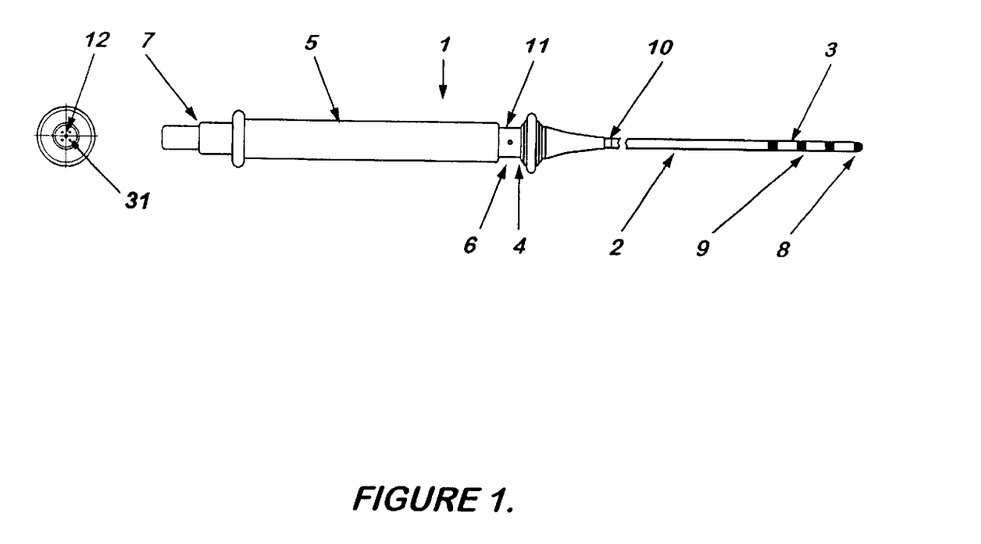
FIG. 1 is an overall view of a steerable ablation catheter system with a disposable catheter shaft constructed in accordance with the principles of the present invention.

Referring to FIG. 1, a steerable ablation catheter 1 constructed in accordance with the principles of the present invention comprises: a catheter shaft 2 having a distal portion, a distal end 3, a proximal end, and a connecting unit 4 at the proximal end; and a handle 5 having a matching connecting unit 6 at its distal end, and a connector 7 at its proximal end. The catheter shaft part and the handle part can be packaged separately, but need to be coupled before use. In a clinical procedure, the connecting unit 4 of the catheter shaft part 2 is quickly coupled and locked to the matching connecting unit 6 of the handle part 5.

An ablation electrode 8 is mounted at the tip of the distal end 3, with at least one mapping electrode 9 disposed on the distal tip section of the catheter shaft. The proximal end of the catheter shaft 2 is equipped with a connecting unit 4. A strain relief 10 is for the catheter tubing to be firmly inserted into the connecting unit 4. The handle 5 comprises a plunger 11 provided for steering mechanisms, a matching connecting unit 6 on the plunger 11, and a connector 7. The steering mechanism can be mechanical, electro-mechanical, electronic or other robotics type operations. The connector 7 connects the electrical wire 12 to an external EKG monitor for electrophysiology mapping, and an energy delivery wire 31 to an external RF generator for providing RF energy to the ablation electrode for cardiac ablation applications. The matching connecting unit 6 of the handle 5 matches the connecting unit 4 of the catheter shaft part 2, with respect to the pairs of steering wires, the conducting wires, and the energy delivery wires. The distal tip section of the catheter shaft is steerably flexible and laterally deflectable into various configurations by using the steering mechanism on the handle. FIG. 1 shows a complete steerable ablation catheter system in its final useable form.

Figure 2:
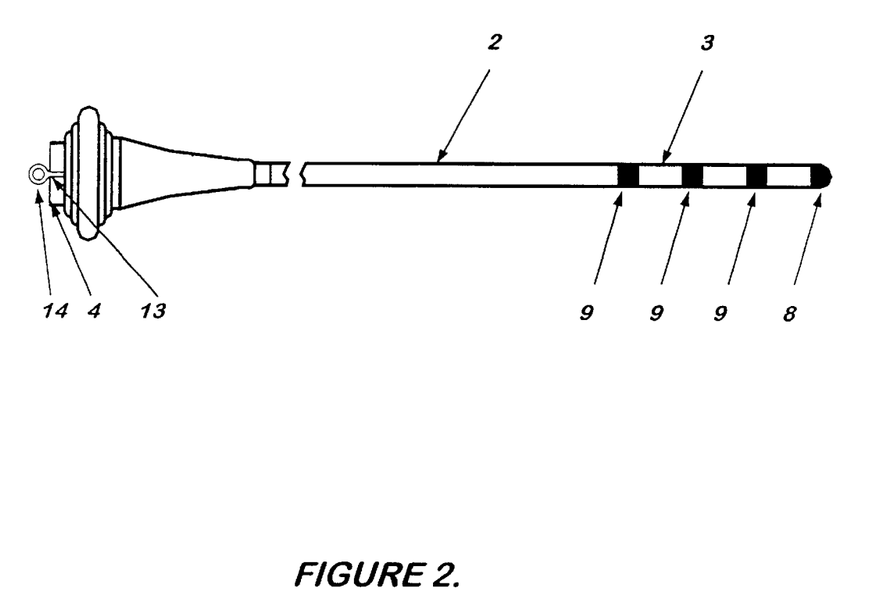
FIG. 2 is a front view of the catheter shaft part of the steerable ablation catheter system of FIG. 1.
Figure 3:
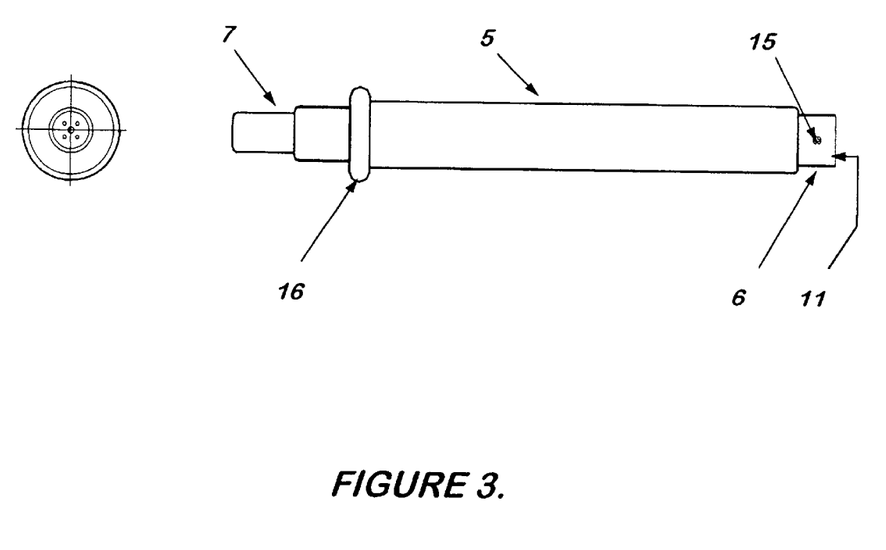
FIG. 3 is a front view of the handle part of the catheter system of FIG. 1.
Figure 4:
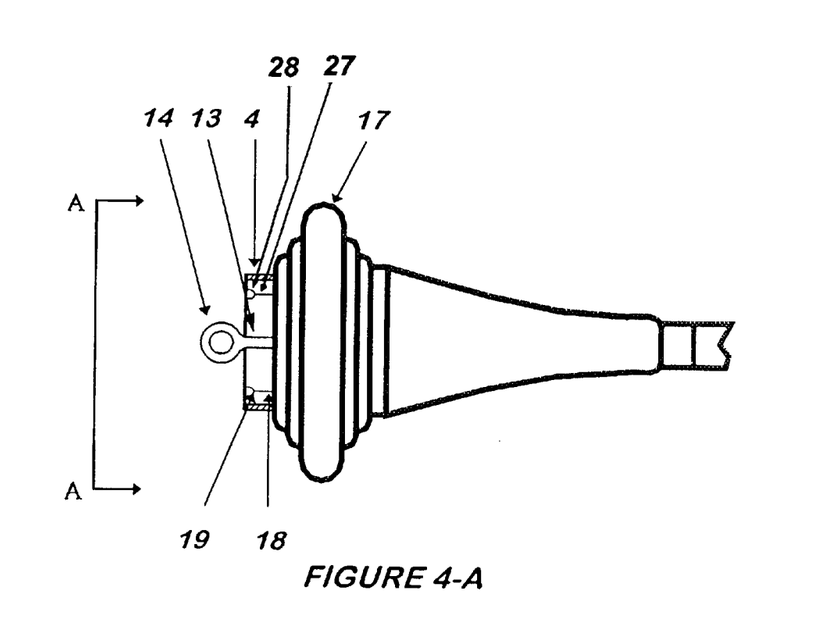
FIG. 4A is a front view of the connecting unit of the catheter shaft part of FIG. 2.
FIG. 4B is a cross-sectional view of FIG. 4A.
FIG. 4C is a close-up view of the steering wire structure of FIG. 4A.

FIG. 2 shows the catheter shaft part 2 of the catheter system 1. The connecting unit 4 of the catheter shaft part 2 has a first steering wire 13 and its corresponding steering wire end 14. The push and pull motion of the first steering wire 13 is to deflect the tip section of the catheter system. The matching connecting unit 6 of the handle part 5 as shown in FIG. 3 is disposed at the distal end of the plunger 11. A set screw 15 in FIG. 3 that sits on the plunger 11 is to quickly couple and lock the first steering wire end 14 securely in place to a second steering wire 26 when the first steering wire end 14 of the connecting unit 4 of the catheter shaft part 2 is inserted into the matching connecting unit 6 of the handle part 5. A palm rest 16 is provided at the proximal end of the handle 5. FIG. 4A is a close-up view of the connecting unit 4 of the catheter shaft part 2 of this invention. A thumb ring 17 is provided in FIG. 4A for a user to push and pull the catheter shaft after the catheter shaft part is connected and locked to the handle. A first conducting wire 18 is connected to one of the mapping electrode 9. A female receptacle 19 of the first conducting wire 18 is to be connected to the male contact 20 of a second conducting wire 23 in the handle part 5 upon intended catheter shaft-to-handle coupling. Similarly, a first energy delivery wire 27, which is connected to one of the ablation electrodes, such as electrode 8, is disposed on the connecting unit 4 of the catheter shaft part 2. A proper receptacle 28 of the first energy delivery wire 27 is to be connected to the matching contact 29 of a second energy delivery wire 30 in the matching connecting unit 6.

FIG. 4B is a cross-sectional view of the proximal end of the catheter shaft part 2. The purpose of the male keyway 22 is to orient the connecting unit 4 in a right position when it is coupled to the matching connecting unit 6 of the handle part 5. A close-up view of the steering wire end 14 is illustrated in FIG. 4C. There is a set screw receptacle 21 in the middle of one side of the first steering wire end 14. This receptacle 21 is provided for the set screw 15 to hold the steering wire end 14 securely in place when coupled to the handle 5.

Figure 5:
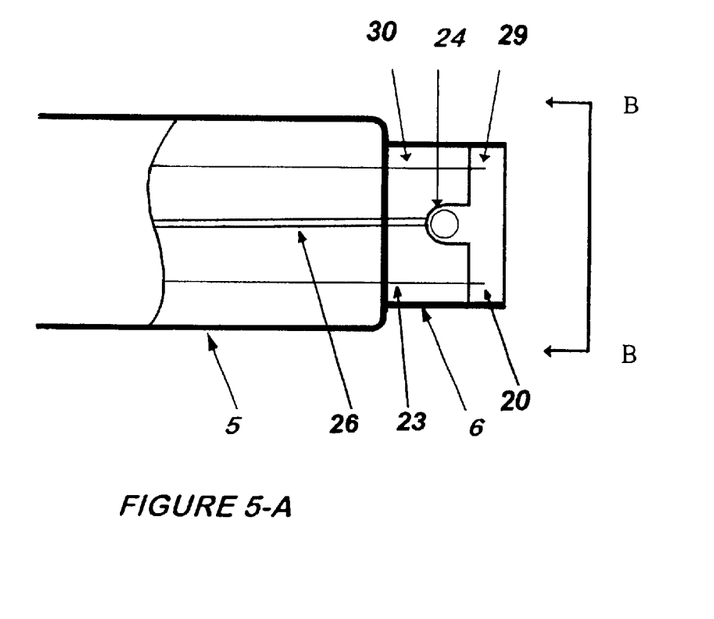
FIG. 5A is a front view of the matching connecting unit of the handle part of FIG. 3.
FIG. 5B is a cross-sectional view of FIG. 5A.

FIG. 5A shows a close-up view of the matching connecting unit 6 of the handle part 5. FIG. 5A has a male contact 20 of a second conducting wire 23, which is to be coupled to the female receptacle 19 of the shaft part 2 upon intended catheter shaft-to-handle coupling. The second conducting wire 23 relays the electrical signals from the catheter shaft part to the connector 7, and externally to an EKG monitor. The tap hole 24 is provided in the center of the matching connecting unit 6 to receive the first steering wire end 14 from the shaft part 2. The set screw 15 is to securely lock the first steering wire end 14 in place when both parts are connected and the set screw is placed into the set screw receptacle 21. Upon unscrewing the set screw 15, the first steering wire end is released from the tap hole 24 and the two parts are separated thereafter for disposal of the catheter shaft.

FIG. 5B is a cross-sectional view of the connecting unit 6. The female keyway 25 on the matching connecting unit 6 is to match the male keyway 22 of the connecting unit 4 so that all pairs of the contacts 19 and 20, 28 and 29, 14 and 24 are squarely matched upon intended catheter shaft-to handle coupling.

The steering control mechanism is positioned at its handle portion. The steerability may rely on at least one steering wire extending from the handle of the catheter to a distal tip of the catheter shaft. The steering wire provides a mechanism for fine deflectable positioning of the electrodes at the distal tip section. At the same time, it improves the torsional stiffness of the catheter shaft. In one embodiment, the catheter system comprises a catheter shaft having a distal portion, a distal end, a proximal end, and at least one central lumen extending therebetween; and a handle at its proximal end.

In a further embodiment, a steerable ablation catheter system comprises a catheter shaft having a distal portion, a distal end, a proximal end, and a central lumen extending therebetween, wherein the distal portion of the shaft is steerably deflectable. The catheter system further comprises a connecting unit located at the proximal end of the catheter shaft, wherein at least one first steering wire extending from the distal end of the shaft through the central lumen of the shaft is disposed at said connecting unit, and wherein said first steering wire has a quick coupling and locking means inside the connecting unit. The catheter system also comprises at least one mapping electrode at the distal portion of the catheter shaft, wherein at least one first conducting wire means for connecting the mapping electrode is disposed at said connecting unit, and wherein said at least one first conducting wire has a quick coupling and locking means inside the connecting unit; and at least one ablation electrode at the distal portion of the catheter shaft, wherein at least one first energy delivery wire means for connecting the ablation electrode is disposed at said connecting unit, and wherein said at least one first energy delivery wire has a quick coupling and locking means inside the connecting unit. The catheter system has a handle having a matching connecting unit at the distal end of said handle, wherein at least one second steering wire, at least one second conducting wire, and at least one second energy delivery wire are disposed at the matching connecting unit, which have quick coupling and locking means inside the matching connecting unit. Furthermore, the catheter system comprises a coupling and de-coupling means, wherein the at least one first steering wire, at least one first conducting wire, and at least one first energy delivery wire in the connecting unit are quickly coupled and locked to the at least one second steering wire, at least one second conducting wire, and at least one second energy delivery wire in the matching connecting unit, respectively, and/or quickly de-coupled. The steering wire is preferably made of a metal alloy having strength, resiliency, and bendability.

In an additional embodiment, the catheter system may also comprises an electro-mechanical steering mechanism with optional programmable steering capabilities on said handle. The mechanical control of the tip deflection by the handle is replaced by an electrical, electro-mechanical, or electronic controlled mechanism, such as step motors on the handle. This electromechanical steering mechanism on the handle becomes feasible since the handle of this invention is exchangeable to a catheter shaft and the handle system having the electromechanical or robotics type steering mechanism can be placed adjacent to the patient's bed. The steering control mechanism may be programmed, manipulated, manually instructed, or modeled via a computer program system, where the deflection signal can be sent to an electrical device, such as a step motor to facilitate fine and recorded movement of the catheter tip via the steering wires or other similar moving means. The recorded position of the catheter tip will facilitate the accurate mapping of the intracardiac electrical potentials and the subsequent accurate ablation procedure.

In an exemplary embodiment, the means for deflecting the distal portion of the steerable ablation catheter comprises at least one steering wire, which is composed of a first steering wire and a second steering wire, along with a support wire. Said steering wire is attached to a radially offset location relative to the central longitudinal axis at the distal end of the deflectable portion of the catheter shaft whereas at least a support wire radially inbetween the steering wires, and means at the proximal end of the shaft for selectively applying tension to the steering wire to cause deflection of the deflectable portion. In certain cases, the function of a support wire can be substituted by a spring coil which is stationary at its proximal end with respect to the shaft.

Usually in another embodiment for a steerable ablation catheter of this invention, the distal portion of the shaft may include at least three radially offset lumens, and wherein the two steering wires and one support wire are disposed in the central lumen of the catheter shaft over a proximal portion thereof; the two steering wires disposed in the radially offset lumens over the distal portion thereof and the support wire disposed in the central lumen.

The means for selectively applying tension comprises a handle, and means for applying torque to the steering wire comprises a rotatable ring or push-pull button disposed on the handle, the ring or button being coupled to the proximal end of the steering wire. A variety of other tension applying mechanisms, such as joy sticks, may also be employed.

In another embodiment, the steerable catheter includes a spring tube, instead of a support wire, disposed coaxially in the central lumen of the deflectable tip and extending into the central lumen of the catheter shaft. The spring tube may be, for example, a stainless steel tube in the central lumen of the deflectable tip extending partially into the distal end of the shaft. The stainless steel tube provides a resilient backbone for the steerable tip, greatly improving torque transmission and kink-resistance.

In a further aspect of the present invention, the connecting unit at the proximal end of the catheter shaft consists of at least one first electrical conducting wire from the mapping electrode, at least one first energy delivery wire from the ablation electrode at the distal end, and at least one first steering wire passing through its individual slot. The steering wire having a bulge ball on the proximal side of the slot prevents the wire from retracting back into the catheter shaft. All the first wires are coupled to the second wires in the matching connecting unit on the handle and relayed to the external instruments or apparatus. In the present invention, the matching connecting unit at the distal end of the handle matches the connecting unit from the proximal end of said catheter shaft. During coupling on the two connecting units together, the gripping mechanism of the second steering wire from the matching connecting unit grips the corresponding first steering wire of the shaft connecting unit. In the meantime, the second electrical wire and energy delivery wire from the matching connecting unit contact their counterparts of the shaft connecting unit. At this time, all the wires from the shaft have been connected to the handle. The steering can be thereafter achieved using any conventional means of steering mechanisms or means of programmable electromechanical steerable mechanism of this invention.

While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A steerable ablation catheter system comprising:
   a catheter shaft having a distal portion, a distal end, a proximal end, and a central lumen extending therebetween, wherein the distal portion of the shaft is steerably deflectable;
   a connecting unit located at the proximal end of the catheter shaft, wherein at least one first steering wire extending from the distal end of the shaft through the central lumen of the shaft is disposed at said connecting unit, and wherein said first steering wire has a quick coupling and locking means inside the connecting unit;
   at least one mapping electrode at the distal portion of the catheter shaft, wherein at least one first conducting wire means for connecting the mapping electrode is disposed at said connecting unit, and wherein said at least one first conducting wire has a quick coupling and locking means inside the connecting unit;
   at least one ablation electrode at the distal portion of the catheter shaft, wherein at least one first energy delivery wire means for connecting the ablation electrode is disposed at said connecting unit, and wherein said at least one first energy delivery wire has a quick coupling and locking means inside the connecting unit;
   a handle having a matching connecting unit at the distal end of said handle, wherein at least one second steering wire, at least one second conducting wire, and at least one second energy delivery wire are disposed at the matching connecting unit, which have quick coupling and locking means inside the matching connecting unit; and
   a coupling and de-coupling means, wherein the at least one first steering wire, at least one first conducting wire, and at least one first energy delivery wire in the connecting unit are quickly coupled and locked to the at least one second steering wire, at least one second conducting wire, and at least one second energy delivery wire in the matching connecting unit, respectively, and/or quickly de-coupled.

2. A steerable ablation catheter system as in claim 1, wherein the at least one second conducting wire is connected to an external EKG monitor.

3. A steerable ablation catheter system as in claim 1, wherein the at least one second energy delivery wire is connected to an external radiofrequency generator.

4. A steerable ablation catheter system as in claim 1 further comprising a support wire, wherein the at least one first steering wire has a distal end, and wherein the distal end of said at least one first steering wire is secured to the support wire.

5. A steerable ablation catheter system as in claim 1, further comprising a push-pull button disposed on the handle, wherein said push-pull button is coupled to the at least one second steering wire of the matching connecting unit.

6. A steerable ablation catheter system as in claim 1, further comprising a rotatable ring disposed on the handle, wherein said rotatable ring is coupled to the at least one second steering wire of the matching connecting unit.

7. A steerable ablation catheter system comprising:
   a catheter shaft having a distal portion, a distal end, a proximal end, and a central lumen extending therebetween, wherein the distal portion of the shaft is steerably deflectable;
   a connecting unit located at the proximal end of the catheter shaft, wherein at least one first steering wire extending from the distal end of the shaft through the central lumen of the shaft is disposed at said connecting unit, and wherein said first steering wire has a quick coupling and locking means inside the connecting unit;
   at least one mapping electrode at the distal portion of the catheter shaft, wherein at least one first conducting wire means for connecting the mapping electrode is disposed at said connecting unit, and wherein said at least one first conducting wire has a quick coupling and locking means inside the connecting unit;
   at least one ablation electrode at the distal portion of the catheter shaft, wherein at least one first energy delivery wire means for connecting the ablation electrode is disposed at said connecting unit, and wherein said at least one first energy delivery wire has a quick coupling and locking means inside the connecting unit;
   a handle having a matching connecting unit at the distal end of said handle, wherein at least one second steering wire, at least one second conducting wire, and at least one second energy delivery wire are disposed at the matching connecting unit, which have quick coupling and locking means inside the matching connecting unit;
   a coupling and de-coupling means, wherein the at least one first steering wire, at least one first conducting wire, and at least one first energy delivery wire in the connecting unit are quickly coupled and locked to the at least one second steering wire, at least one second conducting wire, and at least one second energy delivery wire in the matching connecting unit, respectively, and/or quickly de-coupled, and
   an electromechanical steering mechanism with optional programmable steering capabilities on said handle.

8. A steerable ablation catheter system as in claim 7, wherein the at least one second conducting wire is connected to an external EKG monitor.

9. A steerable ablation catheter system as in claim 7, wherein the at least one second energy delivery wire is connected to an external radiofrequency generator.

10. A steerable ablation catheter system as in claim 7, wherein the electro-mechanical steering mechanisms on the handle further comprises a step motor and a programmable processing unit.

11. A steerable ablation catheter system as in claim 7 further comprising a support wire, wherein the at least one first steering wire has a distal end, and wherein the distal end of said at least one first steering wire is secured to the support wire.

* * * * *